(12) United States Patent
Hack

(10) Patent No.: US 8,568,724 B2
(45) Date of Patent: Oct. 29, 2013

(54) USE OF ANTI-FACTOR XI ANTIBODIES FOR PREVENTION OF THROMBUS FORMATION

(76) Inventor: Erik Hack, Diemen (NL)

( * ) Notice: Subject to any disclaimer, the term of this patent is extended or adjusted under 35 U.S.C. 154(b) by 0 days.

(21) Appl. No.: 13/527,261

(22) Filed: Jun. 19, 2012

(65) Prior Publication Data

US 2012/0259097 A1    Oct. 11, 2012

Related U.S. Application Data

(63) Continuation of application No. 13/000,284, filed as application No. PCT/NL2009/050361 on Jun. 19, 2009, now abandoned.

(60) Provisional application No. 61/073,882, filed on Jun. 19, 2008.

(51) Int. Cl.
 *A61K 39/395* (2006.01)
(52) U.S. Cl.
 USPC .......... 424/145.1; 424/133.1; 424/139.1; 424/146.1; 514/13.7; 514/14.9; 530/387.3; 530/388.1; 530/388.25; 530/388.26

(58) Field of Classification Search
 None
 See application file for complete search history.

(56) References Cited

U.S. PATENT DOCUMENTS 6,391,299 B1 * 5/2002 Blackburn et al. ......... 424/133.1
6,500,660 B1 * 12/2002 Fastrez ..................... 435/231

FOREIGN PATENT DOCUMENTS

WO   WO 2009067660 A    5/2009
WO   WO 2009067660 A2 *  5/2009

OTHER PUBLICATIONS

Fujikawa et al., Biochemistry, 1986, 25:2417-2424.*
Janeway et al., Immunobiology, 3$^{rd}$ edition, 1997, Garland Publishing, pp. 2:2-2:8.*
Stern et al., J. Clin. Invest., 1982, 69:1270-1276.*
Gruber, et al., "Factor XI-dependence of surface-and tissue factor-initiated thrombus propagation in primates", Blood, 2003, 102:953-955.
Tucker, et al., "Inhibition of factor XI decreases thrombin production and prevents vascular occlusion in experimental thrombosis in primates", 2007, 110:235A (meeting abstract).
Gruber, et al., "Antithrombotic factor XI antibody inhibition of the intrinsic pathway", Blood, 2001, 98 (11, pt1:42a (meeting Abstract only).
Sun, Y. et al., "Identification of a factor IX binding site on the third apple domain of activated factor XI", J, Biol Chem, 1996, 271:29023-29028.

* cited by examiner

*Primary Examiner* — Michael Szperka
(74) *Attorney, Agent, or Firm* — Browdy and Neimark, PLLC

(57) ABSTRACT

The present invention relates to binding molecules such as antibodies that specifically bind plasma coagulation factor XI and that inhibit factor XI activation and/or activity. The factor XI-binding molecules of the invention may used in methods for preventing or treating diseases, disorders and/or conditions that are mediated by factor XI activation and/or wherein inhibition of factor XI has a beneficial effect.

7 Claims, No Drawings

USE OF ANTI-FACTOR XI ANTIBODIES FOR PREVENTION OF THROMBUS FORMATION

FIELD OF THE INVENTION

The present invention is in the field of haematology, in particular the field of coagulation. The invention relates to methods for inhibiting the formation of blood clots using binding molecules that specifically bind and inhibit the activation and/or activity of factor XI. The antigen binding molecule may or may not be specific for the activated conformation of factor XI and is preferably used in methods for reducing or preventing thrombus formation on synthetic grafts, atherosclerotic plaques or in other pathological thrombotic and thrombo-embolic processes.

BACKGROUND OF THE INVENTION

Coagulation consists of a humoral and a cellular response. The former leads to the conversion of soluble fibrinogen into insoluble fibrin, the latter consists of activation of platelets leading to a platelet plug. Platelet plugs, fibrin threads and included red blood cells together constitute a blood clot. A key molecule in clot formation is thrombin. This protease converts soluble fibrinogen into the insoluble fibrin, it activates platelets, and converts a number of other factors including factors XI, VIII and V, into active species.

Pathological thrombosis refers to clot formation that is not part of a normal hemostatic process and that may result in disease symptoms. For example, thrombosis on an atherosclerotic plaque in a coronary artery may result in acute myocardial infarction and can be considered as a type of pathological thrombosis. Deep venous thrombosis and thrombosis on vascular grafts are other examples of pathological thrombosis.

Current anticoagulant drugs inhibit the basal pathway of coagulation: heparin (via antithrombin III) hits thrombin, factors Xa and IXa, coumarins inhibit the synthesis of prothrombin, factors VII, IX and X, whereas LMW heparin mainly inhibits factor Xa. The therapeutic window of these drugs is narrow, requiring careful monitoring of patients. Some of the newer anticoagulant drugs under development target at the FVIII/FIX amplification loop.

Considering the severe bleeding tendency resulting from a complete deficiency of factor VIII or IX, in hemophilia A or B, respectively, targeting at this level likely will also require careful monitoring to prevent the risk of bleeding side effects, particularly at overdosing.

Factor XI is not a target for current anticoagulants. This is mainly due to the fact that factor XI deficiency, in contrast to a deficiency of factor VIII or IX, does not result in a severe bleeding tendency. As a matter of fact many factor XI deficient persons never experience a severe bleeding episode. Only two studies have been performed with antibodies, in both cases polyclonal, against factor XI that inhibit the function of factor XI in vivo, either by inhibiting the activity of the molecule or by preventing its activation. In a first study (Minnema et al., 1998, J Clin Invest. 101:10-14) polyclonal antibodies against rabbit factor XI were used to evaluate the effect of factor XI blockade on clot formation in vivo in an experimental thrombosis model in rabbits. Incorporation of anti-factor XI antibodies in jugular vein thrombi resulted in an almost twofold increase in endogenous thrombolysis compared with a control antibody. A similar effect was observed when the anti-factor XI antibody was administered systemically.

The effect of administration of neutralizing polyclonal goat anti-factor XI-antibodies on the accumulation of platelets and fibrin on arterio-venous grafts in baboons was topic of another study to evaluate factor XI as target for antithrombotic therapy (Gruber and Hanson, 2003, Blood 102:953-955). In that study the role of factor XI-dependent thrombus propagation under arterial flow conditions was investigated. Under the conditions used rapid thrombus growth was produced on the grafts of Dacron or Teflon deployed into arteriovenous shunts in baboons treated with anti-human factor XI antibody. Administration of the polyclonal antibodies against factor XI markedly reduced intraluminal thrombus growth on both surfaces. The antithrombotic effect of the polyclonal antibodies against factor XI was found to be comparable with that of heparin at doses that significantly prolonged the partial thromboplastin time, prothrombin time, and bleeding time, whereas anti-FXI antibodies only affected the partial thromboplastin time but not prothrombin time and bleeding time.

There is however still a need in the art for anti-coagulant therapies based on antigen binding molecules that target factor XI.

DESCRIPTION OF THE INVENTION

The present invention relates to means and methods for anti-coagulant therapy that are based on the inhibition of factor XI. The inventors have found that factor XI is a preferred target for inhibition as this leaves coagulation via the "basal" pathway and the FIX/VIII amplification loop intact, which is sufficient for most hemostatic conditions. In other words, factor XI inhibitors have less risk for bleeding side effects. Indeed, factor XI deficiency or factor XI inhibition had no effect on the bleeding time, in contrast to high dose heparin which strongly prolonged bleeding time. These data make factor XI an attractive target for anticoagulant therapy, the more since e.g., severe bleeding complications such as intracerebral hemorrhage rarely occur in persons with factor XI deficiency (F Peyvandi et al., Haematologica 2002; 87:512-514). Thus, because of its active role in pathologic thrombosis and a minor role in normal hemostasis, factor XI is an attractive target for anti-coagulant therapy.

In a first aspect therefore, the present invention relates to a binding molecule that specifically binds to factor XI and that inhibits the functional activity of factor XI.

Factor XI is herein understood as the mammalian plasma coagulation factor XI. In a preferred embodiment a binding molecule of the invention specifically binds to and inhibits the functional activity of at least human factor XI. Plasma coagulation factor XI is a glycoprotein present in human plasma at a concentration of 25-30 nM as a zymogen that when converted by limited proteolysis to an active serine protease, participates in the contact phase of blood coagulation. The sequence of the human factor XI gene has been identified and the deduced amino acid sequence is depicted in SEQ ID NO: 1. The gene for human factor XI is 23 kilobases (kb) in length and consists of 15 exons (I-XV) and 14 introns. Exon I encodes the 5'-untranslated region, and exon II encodes a signal peptide. The next eight exons (III-X) encode four tandem repeat sequences of 90 or 91 amino acids (Apple domains) that are present in the amino-terminal region of the mature protein. The carboxyl-terminal region of the protein, which contains the catalytic serine protease domain, is encoded by five exons (XI-XV) that are interrupted by four introns. Factor XI is a zymogen, which is unique among the other clotting factors in that it exists as a homo-dimer consisting of two identical subunits of 80 kDa connected by a single disulfide bond.

Conversion of zymogen factor XI to the active form, factor XIa, is accomplished by a single cleavage at $Arg_{369}$-$Ile_{370}$ (SEQ ID NO: 1), upon which cleavage each subunit is converted into a 35 kDa light chain and a 50 kDa heavy chain linked by disulfide bonds. The light chain contains a catalytic site. Each heavy chain is composed of four 90-91 amino acid repeats called apple domains (A1-A4) with A1 located at the aminoterminal end of the heavy chain. Thus fully activated factor XI consists of two light chains of 35 kDa and two heavy chains of 50 kDa, and contains two active sites. The A1 domain contains the binding site for high molecular weight kininogen and thrombin. The function of the A2 domain is not clear, initially it was reported to contain an interaction site with factor IX, but later it was shown that this site was located in the A3 domain. The A3 domain also contains a binding site for heparin, and for platelets. The binding sites for factor IX and platelets are close to each other and it has been postulated by Gailani et al. (D Gailani et al., Blood 2001; 97:3117-3122) that this is the reason for the dimeric structure: due to its dimeric structure factor XI can bind via the A3 domain of one subunit to platelets and use its other A3 domain to interact with factor IX. In this way, factor XI can target activation of coagulation to the platelet surface. Finally, the A4 domain of factor XI is involved in dimer formation, contains a free cystein of unknown significance, and an interaction site with factor XIIa. Factor XI can be activated by at least three coagulation proteases, factor XIIa, factor XIa (autoactivation) and thrombin.

A binding molecule of the invention, that can bind to, that has affinity for and/or that has specificity for a factor XI target molecule (or an epitope on the factor XI target molecule) may be said to be "against" or "directed against" said target molecule or antigen. The term "specificity" refers to the number of different types of epitopes or antigenic targets on factor XI to which a particular (antigen-) binding molecule can bind. The specificity of an antigen-binding molecule can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein. Alternatively, the affinity can also be expressed as the affinity constant ($K_A$), which is $1/K_D$. Affinity can be determined in a manner known per se, depending on the specific combination of antigen-binding protein and antigen of interest.

Avidity is herein understood to refer to the strength of binding of a target molecule with multiple binding sites by a larger complex of binding agents, i.e. the strength of binding of multivalent binding. Avidity is related to both the affinity between an antigenic determinant and its antigen-binding site on the antigen-binding molecule and the number of binding sites present on the antigen-binding molecule. Affinity, on the other hand refers to simple monovalent receptor ligand systems.

Typically, factor XI-binding molecules of the invention will bind the target molecule with a dissociation constant ($K_D$) of about $10^{-7}$ to $10^{-12}$ M or less, and preferably $10^{-8}$ to $10^{-12}$ M or less, and/or with a binding affinity of at least $10^{-7}$ M, preferably at least $10^{-8}$ M, more preferably at least $10^{-9}$ M, such as at least $10^{-10}$, $10^{-11}$, $10^{-12}$ M or more. Any $K_D$ value greater than $10^{-4}$ M (i.e. less than 100 μM) is generally considered to indicate non-specific binding. Preferably, a binding molecule of the invention will bind to factor XI with an affinity less than 50, 10 or 5 nM, more preferably less than 1 nM, such as less than 500, 200, 100, 50, 10 or 5 μM. Specific binding of a binding molecule to factor XI can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

The binding molecules of the invention inhibit at least one of the functional activities of factor XI and the activation of factor XI. Preferably, binding molecules of the invention inhibit the functional activity of factor XI and/or inhibit the activation of factor XI, independently of how factor XI is activated. A preferred binding molecule of the invention, e.g., an antibody or antibody fragment, has only one binding site that binds and inhibits factor XI activation or factor XI activity.

In one embodiment, the binding molecule inhibits the functional activity of factor XI by preventing it to become activated.

In a further embodiment, the binding molecule inhibits the activation of factor XI by binding to or near to the peptidyl bond $Arg_{369}$-$Ile_{370}$, and preventing the cleavage of this bond by thrombin, factor XIIa, factor XIa or any other protease. Preferably, upon binding of the binding molecule to factor XI, there is a reduction in the activation of factor XI by factor XIIa, thrombin or factor XIa of at least 60, 70, 80, 90, 95, 99%. More preferably no activation of factor XI by factor XIIa, thrombin or factor XIa, is detectable upon binding of the binding molecule to factor XI.

The amount of reduction in the activation of factor XI may be determined in the various assays as described in the Examples herein by comparing activation of factor XI in the presence of the binding molecule with activation in the absence of the molecule.

In a further embodiment, the binding molecule inhibits the activation of factor XI by binding to the A1 domain of factor XI thereby preventing the interaction of factor XI with high molecular weight kininogen and/or thrombin (B N Bouma et al., Curr Opin Hematol 2000, 7:266-272). Preferably, upon binding of the binding molecule to factor XI, there is a reduction in the activation of factor XI by factor XIIa, thrombin or factor XIa of at least 60, 70, 80, 90, 95, 99%. More preferably no activation of factor XI by thrombin is detectable upon binding of the binding molecule to factor XI. The amount of reduction in the activation of factor XI may be determined in the various assays as described in the Examples herein by comparing activation of factor XI in the presence of the binding molecule with activation in the absence of the molecule.

In a further embodiment, the binding molecule inhibits the activity of factor XI by binding to or near to the active site located in the light chain region of the molecule.

In a further embodiment, the binding molecule inhibits the activity of factor XI by binding to the A2 or A3 domain of factor XI, that are involved in the interaction with factor IX, heparin and or platelets (B N Bouma et al., Curr Opin Hematol 2000, 7:266-272).

In a further embodiment, the binding molecule inhibits the activation of factor XI by binding to or near to sites that are involved in the interaction with its substrate factor IX.

In a further embodiment, the binding molecule preferentially binds to the activated form of factor XI and inhibits the activation of factor XI by binding to or near to sites that are involved in the interaction with its substrate factor IX.

In a further embodiment, the binding molecule preferentially binds to the activated form of factor XI and inhibits the activation of factor XI by binding to the A1 domain of factor XI thereby preventing the interaction of factor XI with high molecular weight kininogen and/or thrombin.

In a further embodiment, the binding molecule preferentially binds to the activated form of factor XI and inhibits the activity of factor XI by binding to or near to sites that are involved in the interaction with its substrate factor IX.

In a further embodiment, the binding molecule preferentially binds to the activated form of factor XI and inhibits the activity of factor XI by binding to or near to the active site located in the light chain region of the molecule.

In a further embodiment, the binding molecule preferentially binds to the activated form of factor XI and inhibits the activity of factor XI by binding to the A2 or A3 domain of factor XI, that are involved in the interaction with factor IX, heparin and or platelets.

The binding molecules of the present invention are thus characterised by their ability to prevent activation and/or inhibit the activity of factor XI and/or to inhibit activation of factor IX. Said inhibitors can be selected by the assessment of their effect in various assays as described in the Examples herein. In particular factor XI-binding molecules can be selected by the assessment of their effect on the clotting activity of the coagulation system as determined with an activated partial thromboplastin time (APTT) in human plasma. The functional properties of factor XI-binding molecules of the invention may be tested by adding these to fresh human plasma, followed by measurement of the APTT in a regular clotting assay. In case of an inhibiting antibody, a prolongation of the APTT will be observed. As controls normal plasma (normal APTT) and factor XI-deficient plasma (prolonged APTT) are tested. These clotting assays are well known in the art (see also Examples herein).

The effects of factor XI-binding molecules on the function of the factor XI molecule can also be tested using chromogenic substrates. Chromogenic substrates consist of small peptides coupled to p-nitroanilide (pNA). Hydrolysis of the substrate releases pNA which can be measured with a spectrophotometer. Specificity of the substrate for certain proteases is dependent on the precise sequence of the peptide linked to pNA. In case of factor XIa, the substrate 52366 (Pyr-Glu-Pro-Arg-pNA-2H2O; Chromogenix, Molndal, Sweden) is appropriate. Measurement of factor XIa activity with this substrate can be done using the method described by Minnema et al. (1998, Blood 92:3294-3301). Factor XI-binding molecules that inhibit the catalytic center of factor XIa can be identified by their inhibiting effect on the chromogenic activity of factor XIa in such a chromogenic activity.

In an alternative method, purified factor XIIa can be used to activate factor XI, which then can be monitored by measuring its chromogenic activity.

Factor XI-binding molecules that inhibit the activation of factor XI by factor XIIa will manifest themselves by decreasing the amount of factor XIa generated in this system.

In one embodiment, a factor XI-binding molecule of the invention that inhibits the functional activity or activation of factor XI preferably is a molecule that produces at least 90% inhibition of factor XI activity at a concentration of about 50-80 nM in an activated partial thromboplastin time (APTT) assay. More preferably the molecule produces at least 95% inhibition of factor XI activity at a concentration of about 50-80 nM in an activated partial thromboplastin time (APTT) assay. Most preferably the molecule produces at least 99% inhibition of factor XI activity at a concentration of about 50-80 nM in an activated partial thromboplastin time (APTT) assay.

In a further embodiment, a factor XI-binding molecule of the invention that inhibits the functional activity or activation of factor XI is a molecule that produces at least 90% inhibition of factor XI activity at a concentration of about 20-50 nM in an activated partial thromboplastin time (APTT) assay. More preferably the molecule produces at least 95% inhibition of factor XI activity at a concentration of about 20-50 nM in an activated partial thromboplastin time (APTT) assay. Most preferably the molecule produces at least 99% inhibition of factor XI activity at a concentration of about 20-50 nM in an activated partial thromboplastin time (APTT) assay.

The term "activator" as used throughout the invention refers to "a molecule capable of activating factor XI in such a way that this subsequently activates factor IX, which in presence of its cofactor FVIII in its turn activates factor X and the rest of the coagulation cascade". Activator molecules include thrombin, factor XIIa and factor XIa.

In a preferred embodiment, a factor XI-binding molecule of the invention is an antibody or a factor XI-binding fragment of an antibody. As used herein, the term "binding molecule" thus encompasses, but is not limited to, an antibody and fragments thereof, a unibody, a diabody, a triabody, a tetravalent or other multivalent antibody specifically binding factor XI and inhibiting the functional activity of factor XI. The term "antibody" refers to polyclonal antibodies, monoclonal antibodies, antibodies which are derived from a phage library, humanized antibodies, human antibodies, synthetic antibodies, chimeric antibodies, single domain antigen binding proteins and antibody fragments such as, but not limited to single-chain Fv's.

Also antibodies made in other animal species such as camelid antibodies or fragments thereof ("Nanobodies") fall within the scope of this application. Furthermore, molecules with antibody-like binding properties such as Designed Repeat Proteins like DARPins (Designed Ankyrin Repeat Proteins) are within the scope of this application.

The factor XI-binding molecule of the invention is a component that specifically binds to the target molecule with a desired binding affinity (as herein defined). The factor XI-binding protein of the invention preferably is a mono-specific antigen-binding protein. A composition comprising a mono-specific antigen-binding protein, is understood to mean a composition having a homogeneous population of the factor XI-binding protein. It follows that the mono-specific factor XI-binding protein is specific for a single epitope on a factor XI monomer. It is however expressly included in the invention that the compositions of the invention may comprise more than one type of mono-specific factor XI-binding protein, each consisting of a homogeneous population. Usually, however, in the context of the present invention, a composition of the invention will not comprise more than 4, 6, 8, 10 or 20 different mono-specific factor XI-binding proteins. The factor XI-binding protein will usually be an antibody or fragment thereof, in which case the mono-specific factor XI-binding protein will thus be a monoclonal antibody or a fragment thereof, which may be obtained from a cloned cell-line (e.g., hybridoma) or expressed from a cloned coding sequence. The term "monoclonal antibody" is thus not intended to be limited by the manner in which it is made. The term mono-specific factor XI-binding protein as used herein thus excludes polyclonal antibodies and antisera.

In addition, any construct of an antibody or a fragment is also a subject of current invention. As used herein, the term "construct" relates to diabodies, triabodies, tetravalent antibodies, pepta- or hexabodies, and the like, that are derived from an anti-human factor XI antibody according to the present invention. Said multivalent antibodies comprising at least one hypervariable domain from an anti-factor XI antibody according to the present invention can be mono-, bi- or multispecific. A preferred antibody or antibody fragment has only one binding site that binds and inhibits factor XI activation or factor XI activity.

As used herein, the term "human antibody", as used herein is intended to include antibodies having variable and constant regions derived from human germline immunoglobulin sequences. The human antibodies may include amino acids residues not encoded by human germline immunoglobulin sequences, e.g., mutations introduced by random or site-specific mutagenesis in vitro or by somatic mutation in vivo.

As used herein, the term "humanized antibody" means that at least a portion of the framework regions of an immunoglobulin or engineered antibody construct is derived from human immunoglobulin sequences. It should be clear that any method to humanise antibodies or antibody constructs, as for example by variable domain resurfacing (Roguska et al., 1994) or CDR grafting or reshaping (Hurle et al., 1994), can be used.

As used herein, the term "chimeric antibody" refers to an engineered antibody construct comprising of variable domains of one species (such as mouse, rat, goat, sheep, cow, lama or camel variable domains), which may be humanized or not, and constant domains of another species (such as non-human primate or human constant domains) (for review see Hurle et al., 1994, supra). It should be clear that any method known in the art to develop chimeric antibodies or antibody constructs can be used.

In one embodiment of the invention, the antibody is an intact murine IgG1, an intact human IgG1 mutated in the constant region to reduce or prevent complement activation or Fc receptor interactions, or an intact human IgG4.

In one embodiment of the invention, the antibody or antibody fragment is a monomeric IgM antibody subunit.

In one embodiment of the invention, the antibody or antibody fragment does not activate the classical or lectin pathways of complement, and/or does not interact with Fc-receptors.

In one embodiment of the invention, the binding molecule is a binding-domain immunoglobulin fusion protein comprising (i) a binding domain polypeptide in the form of a heavy chain variable region or a light chain variable region that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region.

As used herein, in connection with antibodies, the term "fragment" or "fragments" refers to Fab, F(ab')$_2$, Fv, 1scFv, Fd (consisting of the $V_H$ and $C_{H1}$ domains), dAb (consisting of a $V_H$ domain), a complementarity determining region (CDR), e.g., $V_H$ CDR3, and other fragments which retain the antigen binding function and specificity of the parent antibody. The methods for producing said fragments are well known to a person skilled in the art and can be found, for example, in *Antibody Engineering*, Oxford University Press, Oxford (1995/1996) and *Methods in Molecular Biology*, Humana Press, New Jersey (1995).

As used herein, the term "single chain Fv", also termed scFv, refers to engineered antibodies prepared by isolating the binding domains (both heavy and light chains) of a binding antibody, and supplying a linking moiety which permits preservation of the binding function. This forms, in essence, a radically abbreviated antibody, having only that part of the hyper-variable domain necessary for binding the antigen. Determination and construction of single chain antibodies are described in, e.g., U.S. Pat. No. 4,946,778 to Ladner et al.

As used herein the term "single domain antigen binding protein" refers to antibodies or fragments thereof that are derived from antibodies naturally devoid of light chains. Antibodies naturally devoid of light chains may be obtained e.g., by immunization of camelids (e.g., llamas) or sharks (see further below). These antibodies comprise heavy chains only and are devoid of light chains. The advantage of use of such single domain heavy chain antibodies is that they are exceptionally stable even at higher temperatures, small and are easily produced in microbial host organisms such as *Saccharomyces cerevisiae*. Thus, a factor XI-binding protein of the invention preferably comprises an immunoglobulin-derived variable domain that comprises a complete antigen-binding site for an epitope on a target molecule in a single polypeptide chain. Such factor XI-binding proteins specifically include but are not limited to:

(1) antibodies obtainable from camelids and sharks that consist of only heavy chains and that are naturally devoid of light chains;

(2) variable domains of the antibodies defined in 1), usually referred to as VHH domains (see WO2006/040153);

(3) engineered forms of the antibodies defined in 1) or domains in 2) such as e.g., "camelidised" antibodies in which frame work sequences of a camelid (or shark) VHH domain are grafted with CDRs obtained from other sources;

(4) engineered forms of immunoglobuline-like variable domains in which frame works sequences from a variety of immunoglobuline-like molecules are combined with CDRs specific for a given target molecule as e.g., described in WO 04/108749.

Monoclonal antibodies of the present invention can be obtained by isolating immune cells from an animal immunised with human factor XI or with activated human factor XI (factor XIa), or with parts of these molecules, and immortalisation of these cells to yield antibody secreting cell lines such as hybridomas. Cell lines that produce the desired antibodies can be identified by screening culture supernatants for the presence of antibody activity, and by establishment of the effect of the selected antibody on the functional activity of factor XI.

Human factor XI, factor XIa, fragments thereof and/or synthetic peptides comprising factor XI amino acid sequences, isolated according to a variety of purification methods may be used to immunise an appropriate host animal.

A variety of immunization protocols may be employed, and may consist of intravenous, subcutaneous, or intraperitoneal immunization, followed by one or more boosts. A suitable adjuvant is Freund's adjuvant. The precise schedule of administration of the human factor XI, factor XIa, or fragments thereof to the host animal in general is not well defined. The choice of the immunization procedure is more dependent on host animal antibody responses to the administered factor XI, as measured by a suitable assay (vide supra). A suitable immunization procedure, however, is hyperimmunization with human factor XI, or factor XIa, or fragments thereof at a concentration that, dependent on the host animal, may be in the range of 10 to 500 microgram, mixed with Freund's complete adjuvant. The mix is injected subcutaneously. Injections are repeated 2 to 5 times using the same factor XI preparation mixed with Freund's incomplete adjuvant. Blood samples are taken from the animal 1 week after the $3^{rd}$, $4^{th}$, $5^{th}$ injection, and screened for the presence of antibodies against factor XI. In a scheme as indicated above, the length of the interval between the injections can be varied. Alternative adjuvants can also be used.

Alternatively, lymphocytes, human or murine or other, may be immunised in vitro, as for example can be achieved via a procedure outlined by Voss B, 1986 and in EP 8610791.6. Other procedures have also been described: (Luben et al., 1980; Reading, 1986; Reading, 1982). As a source of human lymphocytes, those obtained from patients with antibodies against human factor XI can be used, for example from persons deficient for factor XI who have developed antibody responses against administered exogenous factor XI (O Salomon et al., *Blood* 2003;101:4783-88).

An alternative approach for immunization comprises the use of synthetic peptides that mimic the sequence of functional sites of factor XI, such as individual apple domains. The methods of making antibodies against peptides are well-known in the art and generally require coupling of the peptides to a suitable carrier molecule, for example bovine serum albumin or keyhole limpet hemocyanin. The peptides can be made according to procedures well known in the art. The procedure also may use commercially available peptide synthesiser machines.

Also the hybridoma cell line that produces the antibody may be used as a source of DNA or mRNA encoding the desired antibody, which may be isolated and transferred to cells by known genetic techniques to produce genetically engineered antibody.

The initial screening step of culture supernatants of hybridomas obtained by fusion of lymphocytes of mice immunised with factor XI, factor XIa, parts thereof, or with factor XI peptides, with an appropriate fusion partner, is preferably done by an enzyme-linked immunosorbent assay (ELISA) or a radioimmunoassay (RIA). Both assays are known to those skilled in the art, and consist of coupling of human factor XI or factor XIa to a solid-phase matrix, and assaying for antibody binding to factor XI or factor XIa by a second, labelled antibody. In case peptides are used for immunization, peptides coupled to a solid-phase matrix, also can be used in these assays.

The preferred assay is an enzyme-linked sorbent assay in which purified human factor XI or factor XIa (J F Tait et al., *J Biol Chem* 1987; 262:11651-56) is used for coating, and which is further carried out according to the procedure described by (Smeenk R T J, et al. 1987, *Arthr Rheum* 30: 607), which comprises an incubation step with the hybridoma supernatants and an incubation step with the labeled anti-mouse immunoglobulin reagent.

Subsequently, an alternative screening procedure may be used to assess whether the selected antibody may bind factor XI or factor XIa in solution. This is achieved by a method in which an anti-immunoglobulin agent is coupled to a solid-phase matrix, and bound antibodies against factor XI or factor XIa are specifically detected using labelled purified factor XI or factor XIa. A suitable radioimmunoassay procedure for screening anti-factor XI or anti-factor XIa antibodies may be that described for detection of anti-C3 antibodies by (Hack et al., *J. Immunol.* 1988; 141:1602-9). Alternatively, solutions containing human factor XI or factor XIa may be incubated with the antibody coupled to a solid-phase matrix via an anti-immunoglobulin reagent. The matrix is then washed, and bound factor XI or factor XIa is dissociated from it. The eluted factor XI or factor XIa is then detected by SDS-PAGE followed by Western blotting.

Monoclonal antibodies can also be produced in various other ways with techniques well understood by those having ordinary skill in the art. Details of these techniques are described in (*Antibodies: A Laboratory Manual*, Harlow et al., Cold Spring Harbor Publications, p. 726, 1988), or are described by (Campbell, A. M., *Monoclonal Antibody Technology Techniques in Biochemistry and Molecular Biology*, Elsevier Science Publishers, Amsterdam, The Netherlands, 1984) or by (St. Groth et al., *J. Immunol. Methods* 35:1-21, 1980). These other techniques include, but are not limited to techniques for recombinant production of monoclonal antibodies.

Monoclonal antibodies of any mammalian species, including humans, can be used in this invention. Accordingly, the antibodies according to this embodiment may be human monoclonal antibodies. Such human monoclonal antibodies may be prepared, for instance, by the generation of hybridomas, derived from immunised transgenic animals, containing large sections of the human immunoglobulin (Ig) gene loci in the germline, integrated by the yeast artificial chromosomal (YAC) technology (Mendez et al., 1997).

Furthermore, reference may be made to (Lonberg et al., 1995) and U.S. Pat. No. 5,625,126; U.S. Pat. No. 5,633,425; U.S. Pat. No. 5,569,825; U.S. Pat. No. 5,661,016; and U.S. Pat. No. 5,545,806.

Suitable methods for the production of human monoclonal antibodies have been described in WO 04/035607 (Genmab) and WO 04/043989 (Medarex). Further similar methods have been described in WO 03/017935 (Genmab), WO 02/100348 (Genmab), WO 02/064634 (Medarex) and WO 03/040169 (Medarex).

Fully human antibodies which recognise a selected epitope can also be generated using a technique referred to as "guided selection". In this approach a selected non-human monoclonal antibody, e.g., a mouse antibody, is used to guide the selection of a completely human antibody recognising the same epitope (Jespers et al., 1994).

Additionally, recombinant antibodies, such as chimeric and humanized monoclonal antibodies comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region, see e.g., U.S. Pat. No. 4,816,567; and U.S. Pat. No. 4,816,397. Humanized antibodies are antibody molecules from non-human species having one or more complementarily determining regions from the non-human species and a framework region from a human immunoglobulin molecule, see e.g., U.S. Pat. No. 5,585,089. Such chimeric and humanized monoclonal antibodies can be produced by recombinant DNA techniques known in the art, for example using methods described in WO87/02671; EP 184187; EP 171496; EP 173494; WO 86/01533; U.S. Pat. No. 4,816,567; EP 125023; Better et al., 1988; Liu et al., 1987; Liu et al., 1987; Sun et al., 1987; Nishimura et al., 1987; Wood et al., 1985; and Shaw et al., 1988; Morrison, 1985; Oi et al., 1986; U.S. Pat. No. 5,225,539; Jones et al., 1986; Verhoeyen et al., 1988; Beidler et al., 1988; and Kwon et al., 2002.

Moreover, the present invention also comprises antibodies in which one or more alterations have been made in the Fc region in order to change functional or pharmacokinetic properties of the antibodies. Such alterations may result in a decrease or increase of C1q binding and CDC (complement dependent cytotoxicity) or of FcγR binding and antibody-dependent cellular cytotoxicity (ADCC). Substitutions can for example be made in one or more of the amino acid positions 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624,821 and U.S. Pat. No. 5,648,260. Further reference may be had to WO 00/42072 disclosing antibodies with altered Fc regions that increase ADCC, and WO94/29351 disclosing antibodies having mutations in the N-terminal region of the CH2 domain that alter the ability of the antibodies to bind to FcR and thereby decreases the ability of the antibodies to bind to C1q which in turn decreases the ability of the antibodies to fix complement. Alterations which prevent or reduce the complement activation via the constant region of the antibodies are especially preferred.

The antibodies of the present invention can be prepared by using a technique which provides for the production of antibody molecules by continuous cell lines in culture. These include but are not limited to the hybridoma technique originally described by Kohler and Milstein (Kohler et al., 1975).

Human antibodies of the invention also can be produced in a host cell transfectoma using, for example, a combination of recombinant DNA techniques and gene transfection methods as is well known in the art, see e.g., (Morrison, 1985).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell.

The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or beta-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. No. 4,399,216, U.S. Pat. No. 4,634,665 and U.S. Pat. No. 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, lipofectin transfection and the like.

In one embodiment the antibodies are expressed in eukaryotic cells, such as mammalian host cells. Preferred mammalian host cells for expressing the recombinant antibodies of the invention include CHO cells (including dhfr-CHO cells, described in (Urlaub et al., 1980), used with a DHFR selectable marker, e.g., as described in (R. J. Kaufman et al., 1982), NS/0 myeloma cells, COS cells, HEK293 cells and SP2.0 cells. In particular for use with NS/0 myeloma cells, another preferred expression system is the GS (glutamine synthetase) gene expression system disclosed in WO87/04462, WO89/01036 and EP 338841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Alternatively the cloned antibody genes can be expressed in other expression systems, including prokaryotic cells, such as microorganisms, e.g., *E. coli* for the production of scFv antibodies, algi, as well as insect cells. Furthermore, the antibodies can be produced in transgenic non-human animals, such as in milk from sheep and rabbits or eggs from hens, or in transgenic plants. See e.g., Verma, et al., 1998; Pollock et al., 1999; and Fischer et al., 1999.

Additional information concerning the generation, design and expression of recombinant antibodies can be found in (Mayforth, *Designing Antibodies*, Academic Press, San Diego (1993)).

Regardless of the nature of the antibody, polyclonal, monoclonal, or recombinant, it may be purified by standard techniques well known in the art. Most of these techniques use affinity chromatography, often in combination with a precipitation step.

Cell lines that secrete antibody against human factor XI or factor XIa can be identified by assaying culture supernatants, ascitic fluid, etc., for the presence of antibody. The preferred screening procedure comprises two sequential steps, the first being identification of hybridomas that secrete mAb against human factor XI or factor XIa, the second being determination of the ability of the mAb to inhibit the activation or the functional activity of factor XI and to prevent or reduce activation of factor IX and the rest of the coagulation system. Factor XI-binding diabodies, triabodies, tetravalent antibodies of the invention can be produced by the following methods: 1) chemical linkage of anti-factor XI antibodies of the present invention or univalent fragments thereof following a method as described by e.g., (Fanger M W, Morganelli P M, Guyre P M. Bispecific antibodies. Crit. Rev Immunol. 1992; 12:101-24); 2) genetically engineering of non-covalently-linked diabodies as described by e.g., (Holliger P, Prospero T, Winter G. "Diabodies": small bivalent and bispecific antibody fragments. *Proc Natl Acad Sci USA*. 1993; 90:6444-8) and tetravalent antibodies as described by e.g., (Pack P, Muller K, Zahn R, Pluckthun A. Tetravalent miniantibodies with high avidity assembling in *Escherichia coli*. J Mol. Biol. 1995; 246:28-34); 3) single chain antibodies fused to protein A or Streptavidin as described by e.g., Kipriyanov et al., "Affinity enhancement of a recombinant antibody: formation of complexes with multiple valency by a single-chain Fv fragment-core streptavidin fusion." *Protein Eng.* 1996; 9:203-11) and bispecific tetravalent antibodies as described in e.g., EP 0517024 to Bosslet and Seeman; 4) genetically engineering of triabodies as described by e.g., Kortt et al., "Triabodies: single chain Fv fragments without a linker form trivalent trimers." *FEBS Lett.* 1997; 409:437-41); 5) phage display of Ab combinatorial libraries resulting in the production of high-affinity antibodies and screening of random DNA sequence phage display libraries for small antigen-binding peptides as described in e.g., U.S. Pat. Nos. 5,403,484 and 5,571,698 and 5,223,409; McGuinness et al., "Phage diabody repertoires for selection of large numbers of bispecific antibody fragments." *Nat. Biotechnol.* 1996; 14:1149-54; Hoogenboom HR. "Designing and optimizing library selection strategies for generating high-affinity antibodies." *Trends Biotechnol.* 1997; 15:62-70); and, 6) generation of hybridomas, derived from immunised transgenic mice, containing large sections of the human immunoglobulin (Ig) gene loci in the germ line, integrated by the yeast artificial chromosomal (YAC) technology, resulting in effective blocking antibodies as described by e.g., Mendez et al., 1997, *Nat. Genet.* 15:146-56 (Erratum in: *Nat Genet.* 1997, 16:410).

In a second aspect, the invention relates to methods of preventing or treating a disease, disorder and/or condition that is mediated by factor XI activation and/or wherein inhibition of factor XI has a beneficial effect. The methods preferably comprise the step of administering to a subject a binding molecule as disclosed herein above, in an amount effective to treat or prevent the disease, disorder and/or condition.

Also in this aspect, the invention also relates to the use of a binding molecule as disclosed herein above for the preparation of a medicament for preventing or treating a disease, disorder and/or condition that is mediated by factor XI activation and/or wherein inhibition of factor XI has a beneficial effect.

In this aspect the invention alternatively relates to a binding molecule as disclosed herein above, for use in preventing or treating a disease, disorder and/or condition that is mediated by factor XI activation and/or wherein inhibition of factor XI has a beneficial effect.

In one embodiment a disease, disorder and/or condition that is mediated by factor XI activation and/or wherein inhibition of factor XI has a beneficial effect is disease, disorder and/or condition in which coagulation is involved, such as e.g., a thrombo-embolic or inflammatory disease mediated by coagulation activation via factor XI. Thus, in this embodiment the binding molecules of the invention may be used in a treatment for reducing or preventing thrombus formation and/or its complications.

According to another embodiment the binding molecules of the present invention can be used for inhibiting coagulation in various human diseases. As a result the inhibitors of the present invention can be used for the preparation of a medicament for attenuating thrombo-embolic disorders by inhibiting coagulation in vivo. The binding molecules can be used alone or in combination with other drugs.

In a further embodiment the binding molecules of the present invention can be used alone or in combination with other drugs in any suitable ratios, for the preparation of a medicament to treat a subject suffering of a disease or disease symptoms resulting from pathologic thrombosis and or embolism, or at risk with respect to such a disease.

The present binding molecules inhibit factor XI-dependent amplification of coagulation or factor XI-dependent coagulation by inhibiting the activation and or activity of factor XI. They are therefore suitable for the prevention or treatment of disorders, diseases and conditions in which coagulation is involved. These disorders, diseases and conditions include e.g., (acute) myocardial infarction, ischemic stroke, cardioembolism due to atrial fibrillation, vascular access thrombosis, deep venous thrombosis, arterial thrombosis, coronary artery thrombosis, atherosclerosis, arthritis, vasculitis, respiratory distress syndrome, pulmonary embolism, thrombo-embolism resulting from surgery such as prostate surgery, orthopaedic surgery, such as e.g., hip and knee-replacement, thrombo-embolism resulting from immobilization, thrombosis and occlusion of synthetic grafts, stents, or AV-fistula, diffuse intravascular coagulation (DIC), hemodialysis, atrial fibrillation, sepsis, septic shock, organ failure, kidney failure, toxicity induced by the in vivo administration of therapeutic proteins (e.g., cytokines or mAbs), multiple trauma, ischemia-reperfusion injuries and local undesired fibrin deposition such as e.g., fibrin deposition in the lung alveoli during adult respiratory distress.

Thus, in the present invention, patients suffering from a disease involving coagulation-mediated damage can be administered an effective amount of a monoclonal antibody against factor XI, or fragments a monoclonal antibody against factor XI as described so that activation of factor XI is inhibited. By "effective amount" is meant a concentration of the binding molecule, which is capable of inhibiting coagulation activation.

Treatment (prophylactic or therapeutic) will generally consist of administering a binding molecule of the invention parenterally, preferably intravenously, intraarterially, intramuscularly or subcutaneously. Gruber and Hanson (Gruber and Hanson, 2003, Blood 102:953-955) administered goat anti-factor XI antibodies at a dose of 16-50 mg per kg to achieve sufficient inhibition of factor XI in baboons. In contrast, the dose and administration regimen of a binding molecule of the invention preferably is in the range of a dosage that is equivalent to a dosage of 0.5-20 mg of IgG per kg body weight per week. More preferably, a binding molecule of the invention is administered at a dosage that is equivalent to a dosage of less than 18, 16, 14, 12, 10 8, 6 or 4 mg of IgG per kg body weight per week and/or at a dosage that is equivalent to a dosage of at least 0.6, 0.8, 1.0, 1.2, 1.5, 2, or 4 mg of IgG per kg body weight per week. It is understood that in case of e.g., antibody fragments the dosage to be used will be the molar equivalent of the corresponding amount of mg of an IgG molecule per kg body weight as indicated.

It is further understood that the dosage regimes for the binding molecules of the invention are based on the average serum half-life of a human antibody of about 7 days. The skilled person will know how to adjust the dosage regime of binding molecules with a half-life that is shorter or longer than 7 days.

A further factor that influences the dosage regime for a given binding molecule of the invention is its affinity for factor XI. For example, a binding molecule having a Kd of about 1 nM requires a serum level of about 100 nM to produce 99% factor XI inhibition and a binding molecule having a Kd of about 0.1 nM requires a serum level of about 35 nM to produce 99% factor XI inhibition. On the other hand, 95% factor XI inhibition may be achieved with a binding molecule having a Kd of about 1 nM at a serum level of about 50 nM or at 27 nM with a binding molecule having a Kd of about 0.1 nM. Table 1 shows dosage regimes for anti-factor XI-binding molecule per kg of body weight as function of Kd and interval between administrations.

TABLE 1

Dose of anti/FXI mAb (intact antibody) per kg of body weight as function of Kd and interval between administrations for intact human IgG with a half life of 7 days required for 99% inhibition of circulating factor XI.

| Interval between administrations | Dose (mg-kg) | | |
| --- | --- | --- | --- |
| | Kd 0.1 nM | Kd 1 nM | Kd 10 nM |
| Minimal plasma level mAb to achieve 99% inhibition | 35 nM (=0.005 mg/ml) | 125 nM (=0.02 mg/ml) | 1025 nM (=0.2 mg/ml) |
| 1 week | 0.5 mg/kg[1] | 2 mg/kg | 10 mg/kg |
| 2 weeks | 1 mg/kg | 4 mg/kg | 20 mg/kg |
| 3 weeks | 2 mg/kg | 8 mg/kg | 40 mg/kg |
| 4 weeks | 4 mg/kg | 16 mg/kg | 80 mg/kg |

[1]mg/kg body weight

In a further embodiment, the binding molecule is administered at a dosage wherein the inhibition of factor XI activation in a human body fluid is measurable as at least one of (a) substantially complete blockade of factor IX activation in the body fluid; and (b) a substantially complete blockade of thrombin generation in the body fluid. A substantially complete blockade of factor IX activation and/or of thrombin generation is herein understood as factor IX activation and/or thrombin generation being reduced to less than 1% of the amount of factor IX activation and of thrombin generation in the absence of the binding molecule in the body fluid.

An administered dosage that effects substantially complete blockade of factor IX activation and/or of thrombin generation preferably is a dosage that yields a molar ratio in the body fluid that is equal to or less than 35, 4, or 1 moles of factor XI binding sites of the binding molecule to 1 mole of factor XI, wherein the factor XI binding sites of the binding molecule have a Kd that is equal to or less than 10 nM, 1 nM, or 0.1 nM, respectively. The body fluid is herein understood to be blood, plasma or serum.

The skilled person will know how to adjust the dosage regimes in Table 1 for binding molecules with a half-life that is shorter or longer than 7 days, with a $M_w$ different from human IgG, with a Kd different from 10 nM, 1 nM or 0.1 nM and/or to achieve another percentage of inhibition of circulating factor XI.

In a further embodiment, a binding molecule of the invention, when administered to a human patient via intravenous infusion, provides complete inhibition of factor XI at dosages below 0.005 or 0.003 g/kg.

In a further embodiment, a binding molecule of the invention, when administered to a human patient via intravenous infusion, provides therapeutic benefits at dosages below 0.005 or 0.003 g/kg.

In a further embodiment a binding molecule of the invention is modified to achieve a desired in vivo serum half life. For this purpose a polyalkyleneglycol group (e.g., polyethylene glycol (PEG) group, polypropylene glycol, polybutylene glycol) or a serum protein such as e.g., serum albumin or transferrin can be linked or conjugated to the binding molecule and/or the amino acid sequence of the binding molecule can be modified. In particular the amino acid sequence of the constant domains of a binding molecule that is an antibody can be modified (e.g., introducing amino acid substitutions, deletions and/or insertions). These modifications be thus be used to achieve an in vivo serum half life of the binding molecule of more than 20 days, 10 to 20 days, 5 to 10 days, 1 to 5 days or less than 24 hours.

In one embodiment, the equivalent of the above-indicated weekly dosages of the binding molecules according to the invention can be administered by infusion. Such administration can be repeated as many times as desired. The administration may be performed by bolus injection or infusion or continuous infusion over a period of from less than 2 hours to 24 hours, such as from 2 to 12 hours. In another embodiment, the binding molecules of the invention can be administered by slow continuous infusion over a long period, such as more than 24 hours.

Such regimen may be continued or repeated one or more times as necessary, for example, after 6 months or 12 months. The dosage can be determined or adjusted by measuring the amount of circulating factor XI-binding molecules of the invention antibodies upon administration in a biological sample by using anti-idiotypic antibodies which target the factor XI-binding molecules of the invention. In yet another embodiment, the antibodies can be administered by maintenance therapy, such as, e.g., once a week for a period of 6 months or more.

In one embodiment, the binding molecule of the invention is used in the prevention or reduction of thrombosis (and occlusion) of synthetic grafts, stents, or AV-fistula in e.g., kidney-patients undergoing regular dialysis. In this group of patients the binding molecule may be administered at least weekly or several times (e.g., 2, 3 or 4) per week, preferably when the patients are undergoing dialysis. In a preferred embodiment, the binding molecule is administered to the patient through the dialysis apparatus, e.g., in the dialyzed body fluid that is returned to the patient.

In another embodiment, the binding molecule of the invention is administered in patient with no regular parenteral access that require nonetheless continuous anticoagulant therapy, such as e.g., in patients with atrial fibrillation, unstable angina pectoris, deep venous thrombosis, diffuse intravascular coagulation, prostate surgery, orthopaedic surgery, particularly of the hip, and other thrombo-embolic disorders. In these patients preferably a certain number of administrations of the binding molecule per time period is applied, e.g., once per 2, 3, 4 or 6 weeks. In such instances the binding molecule preferably has a half life of at least 6, 7, 8, 10, 12 or 14 days and a Kd that is less than 1 nM, preferably less than 0.5 nM, and most preferably less than 0.1 nM.

For parenteral administration, the binding molecule will be formulated in an injectable form combined with a pharmaceutically acceptable parenteral vehicle. Such vehicles are well-known in the art and examples include saline, dextrose solution, Ringer's solution and solutions containing small amounts of human serum albumin Typically, the monoclonal antibody or fragments thereof will be formulated in such vehicles at a concentration of from about 20 mg to about 100 mg per ml. In one embodiment of this invention the binding molecule is administered by intravenous injection.

It should be understood that intended to come within the scope of this invention is virtually every method of administering monoclonal antibodies or fragments thereof as described by the present invention, to yield sufficiently high levels either in the circulation or locally.

In a third aspect, the invention relates to a pharmaceutical composition comprising a binding molecule as disclosed herein above and a pharmaceutically acceptable carrier. The pharmaceutical compositions may be formulated with pharmaceutically acceptable carriers or diluents as well as any other known adjuvants and excipients in accordance with conventional techniques such as those disclosed in (Remington: The Science and Practice of Pharmacy, $19^{th}$ Edition, Gennaro, Ed., Mack Publishing Co., Easton, Pa., 1995).

The pharmaceutical compositions according to the invention may be formulated in accordance with routine procedures for administration by any route, such as oral, topical, parenteral, sublingual, transdermal or by inhalation. The compositions may be in the form of tablets, capsules, powders, granules, lozenges, creams or liquid preparations, such as oral or sterile parenteral solutions or suspensions or in the form of a spray, aerosol or other conventional method for inhalation.

The term "pharmaceutically acceptable carrier" relates to carriers or excipients, which are inherently nontoxic and non-therapeutic. Examples of such excipients are, but are not limited to, saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

The pharmaceutical composition may be administered by any suitable route and mode. As will be appreciated by the skilled artisan, the route and/or mode of administration will vary depending upon the desired results. The pharmaceutical compositions of the present invention include those suitable for oral, nasal, topical (including buccal and sublingual), rectal, vaginal and/or parenteral administration.

Formulations of the present invention which are suitable for vaginal administration include pessaries, tampons, creams, gels, pastes, foams or spray formulations containing such carriers as are known in the art to be appropriate.

Dosage forms for the topical or transdermal administration of compositions of this invention include powders, sprays, ointments, pastes, creams, lotions, gels, solutions, patches and inhalants.

The pharmaceutical composition is preferably administered parenterally. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In one embodiment that pharmaceutical composition is administered by intravenous or subcutaneous injection or infusion.

In one embodiment the antibody of the invention are administered in crystalline form by subcutaneous injection, cf. (Yang et al., 2003 *Proc Natl Acad Sci USA* 100:6934-39).

Regardless of the route of administration selected, the compounds of the present invention, which may be used in the form of a pharmaceutically acceptable salt or in a suitable hydrated form, and/or the pharmaceutical compositions of the present invention, are formulated into pharmaceutically acceptable dosage forms by conventional methods known to those of skill in the art.

As used herein, "pharmaceutically acceptable carrier" includes any and all solvents, dispersion media, coatings, antibacterial and antifungal agents, isotonicity agents, antioxidants and absorption delaying agents, and the like that are physiologically compatible.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated.

Preferably, the carrier is suitable for parenteral administration, e.g., intravenous or subcutaneous injection or infusion.

Pharmaceutical compositions typically must be sterile, non-pyrogenic and stable under the conditions of manufacture and storage. The composition can be formulated as a solution, microemulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonicity agents, such as sugars, polyalcohols such as mannitol, sorbitol, glycerol or sodium chloride in the compositions. Pharmaceutically-acceptable antioxidants may also be included, for example (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients e.g., as enumerated above, as required, followed by sterilization microfiltration. Generally, dispersions are prepared by incorporating the active compound into a sterile vehicle that contains a basic dispersion medium and the required other ingredients e.g., from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

If appropriate, the binding molecule may be used in a suitable hydrated form or in the form of a pharmaceutically acceptable salt. A "pharmaceutically acceptable salt" refers to a salt that retains the desired biological activity of the parent compound and does not impart any undesired toxicological effects (Berge, S. M., et al., (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylene-diamine, N-methylglucamine, chloroprocaine, choline, diethanolamine, ethylenediamine, procaine and the like.

Depending on the route of administration, the active compound, i.e., binding molecule, may be coated in a material to protect the compound from the action of acids and other natural conditions that may inactivate the compound. For example, the compound may be administered to a subject in an appropriate carrier, for example, liposomes. Liposomes include water-in-oil-in-water CGF emulsions as well as conventional liposomes (Strej an et al., J. Neuroimmunol. 1984; 7:27).

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

The pharmaceutical compositions can be administered with medical devices known in the art.

For example, in a preferred embodiment, a therapeutic composition of the invention can be administered with a needleless hypodermic injection device, such as the devices disclosed in U.S. Pat. No. 5,399,163, U.S. Pat. No. 5,383,851, U.S. Pat. No. 5,312,335, U.S. Pat. No. 5,064,413, U.S. Pat. No. 4,941,880, U.S. Pat. No. 4,790,824, or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In a further embodiment, the binding molecules of the invention can be formulated to prevent or reduce their transport across the placenta. This can be done by methods known in the art, e.g., by PEGylation of the antibodies or by use of $F(ab')_2$ fragments. Further references can be made to (Cunningham-Rundles C et al., 1992); and to (Landor, 1995).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Materials

Human factor XI, factor XIa, factor XII, beta-factor XIIa, factor IX were obtained from Kordia Life Science, Leiden, the Netherlands. The purity was determined on 12% SDS-PAGE using silver staining.

S299 (Methyl-sulfonyl-D-cyclo-hexylglycyl-glycyl-arginine-p-nitroanilide) was from American Diagnostics (Greenwich, Conn.), and S2366 (L-pyroglutamyl-L-prolyl-L-arginine-p-nitroanilide) was from Diapharma (West Chester, Ohio).

Aprotinin and p-aminobenzamidine (pAB) were from Sigma (St. Louis, Mo.).

Example 1

Chromogenic Assay for Factor XIa

A mixture of 75 μL phosphate-buffered saline (PBS), pH 7.4, containing the chromogenic substrate S-2366 1 mmol/L (final concentration), 5 μL of factor XIa at different final concentrations (range, 0.01-10 nmol/L) and 20 μL PBS are added to wells of microtiter plates (Dynatech, Plochingen, Germany). Conversion of the substrate is measured by using a spectrophotometer. Microtiter plates are read on a Multiskan plate reader (Labsystems, Helsinki, Finland) after incubation for various time intervals at room temperature at 405 nm. The effect of monoclonal antibodies on the chromogenic activity is achieved by pre-incubation 5 μL of factor XIa at a final concentration of 1 nmol/L with 20 μL PBS containing various concentrations of monoclonal antibody to be tested for 15 minutes at room temperature. Seventy-five μL of PBS containing S2366 is added and the conversion of the substrate is measured as described above. A reference consisting of various dilutions of factor XIa (0.1-1 nmol/L) is tested as control. In case of antibodies that inhibit the active site of factor XIa, a decrease in the rate of conversion by the standard amount of factor XIa is observed. This assay is assay 1 described in example 8.

Example 2

Chromogenic Assay for Factor XI Activation by Factor XIIa

Five μL of PBS containing 10 nm factor XI is incubated with 5 μL of 1 nMol/L factor XIIa for 30 minutes at room temperature. Thereafter, 75 μL phosphate-buffered saline (PBS), pH 7.4, containing the chromogenic substrate S-2366 1 mmol/L (final concentration), and 15 μL of PBS are added to wells of microtiter plates (Dynatech, Plochingen, Germany). Conversion of the substrate is measured by using a spectrophotometer. Microtiter plates are read on a Multiskan plate reader (Labsystems, Helsinki, Finland) after incubation for various time intervals at room temperature at 405 nm. The effect of monoclonal antibodies on the activation is tested by adding 15 μL of PBS containing the antibody to be tested to the mixture of factor XI and factor XIIa, in a way that first the antibody is added to factor XI, and after 15 minutes incubation factor XIIa is added. Dilutions of factor XIIa are tested as control. Seventy-five μL of PBS containing S2366 are then added and the conversion of the substrate is measured as described above. A reference consisting of various dilutions of factor XIa (0.1-1 nmol/L) is also tested as control. In case of antibodies that inhibit the activation of factor XI, a decrease in the rate of conversion by the amount of factor XIa generated by factor XIIa is observed. This assay is referred to as assay 2 in Table 2.

Example 3

Chromogenic Assay for Factor IX Activation by Factor XIa

This assay is performed essentially as described by T Ogawa et al., J Biol Chem 2005; 280:23523-30. Briefly, factor IX (1000 nM) in 50 mM Tris-HCl pH 7.5 buffer containing 0.1 mg per ml BSA containing 5 mM $CaCl_2$ was activated by addition of factor XIa (1 nM active sites, 0.5 nM protein). At various time points (0-240 minutes), 50 μl aliquots were removed and supplemented with aprotinin (final concentration 15 μM) to inhibit factor XIa. The steady-state kinetics of hydrolysis of S299 (1 mM) by quenched samples was studied in Tris-BSA buffer containing 5 mM $CaCl_2$ and 33% ethylene glycol. Changes in absorbance at 405 nm were measured. Duplicate assays were run. The factor IX concentration tested in the assay was 1000 nM. Generation of factor IXa as a function of time was determined by interpolation from the linear dependence of the initial rate of S299 hydrolysis on known concentrations of factor IXa. Initial steady-state rates of factor IXa formation were determined from slopes of plots documenting linear appearance of factor IXa with time. The effect of monoclonal antibodies in the assay is tested by pre-incubation of factor XIa with an equal volume of monoclonal antibody.

This assay is referred to as assay 3 in Table 2.

Example 4

Clotting Assay for Factor XI

Effect of the monoclonal antibodies on factor XI or factor XIa clotting activity is tested by incubating factor XI or factor XIa with an equal volume of PBS containing 1 to 10 molar excess of antibody versus factor XI. Factor XI clotting activity is then tested with a one-stage clotting assay. These assays are well known to those skilled in the art. These assays are referred to as assay 4 in Table 2 when performed with factor XI, and as assay 5 when performed with factor XIa.

Example 5

Immunization with Human Factor XI or Factor XIa Immunogens and the Production of Hybridomas The following describes the immunization of mice with purified human factor XI with the aim to isolate lymphocytes from the immunised mice and producing murine hybridomas. It will be further appreciated that the procedure can be employed to produce antibodies against factor XI, factor XIa or fragments thereof.

A suitable procedure for immunisation is described by (Hack C E, Paardekooper J, Smeenk R J, Abbink J, Eerenberg A J, Nuijens J H. Disruption of the internal thioester bond in the third component of complement (C3) results in the exposure of neodeterminants also present on activation products of C3. An analysis with monoclonal antibodies. J. Immunol. 1988; 141:1602-9), for C3. A similar procedure is used for factor XI or factor XIa. Briefly, mice are immunised by repeated intraperitoneal injections of 25 μg of purified human factor XI or XIa given at three-week intervals. The first factor XI or XIa gift is mixed with complete Freund's adjuvant, the subsequent with incomplete Freund's adjuvant. Four days after the final boost, spleens are removed from the immunised mice and the splenocytes are fused with the murine myeloma cell-line SP2/0-Ag14, according to the procedure first described by (Kohler G, Milstein C. Continuous cultures of fused cells secreting antibody of predefined specificity. Nature. 1975; 256:495-7), except that feeder cells are replaced by IL-6 Immunised mice are sacrificed and splenocytes teased from the spleens, and washed in serum free Dulbecco's Modified Eagles medium. Similarly, SP2/0-Ag14 myeloma cells are washed, and added to the splenocytes yielding a 5:1 ratio of splenocytes to myeloma cells. The cells are then pelleted, and the supernatant is removed. One ml of a 40% (v/v) solution of polyethylene glycol 1500 is then added dropwise over a 60 sec period, after which the cells are incubated for another 60 sec at 37° C. Nine ml of Dulbecco's Modified Eagles medium is then added with gentle agitation. The cells are pelleted, washed to remove residual polyethylene glycol, and finally plated at a concentration of $10^5$ cells per well in Dulbecco's Modified Eagles medium containing 10% (v/v) fetal calf serum (100 μl per well). After 24 hours, 100 μl of a 2× solution of hypoxanthine/azaserine selection medium is added to each well. At day 4 hypoxanthine/azaserine selection medium is replenished, at day 7 it is replaced by Dulbecco's Modified Eagles medium containing 10% (v/v) fetal calf serum. During all incubations monocyte derived or recombinant human IL-6 is present in the culture at concentrations of approximately 10 pg/ml. About 80% of the wells exhibit cell growth at day 10.

Example 6

Enzyme Linked Immunosorbent Assay for the Detection of Factor XI Antibodies

The wells are screened for the presence of antibody to factor XI or XIa using an enzyme-linked immunosorbent assay, in which purified human factor XI or XIa is used for coating (2 μg/ml in phosphate buffered saline, pH 7.4 [PBS]; 100 μl/well). Residual non-specific binding sites are then blocked by 30 minutes incubation at room temperature with PBS/0.1% (w/v) Tween 20 (PBS-T) containing 0.2% (w/v) gelatin (PBS-TG). Then, after a washing procedure (5 times with PBS-T), the plates are incubated for 60 minutes at 37° C. with 20 μl of hybridoma supernatant together with 80 μl of PBS-TG. Finally, bound murine antibodies are detected by incubation with peroxidase-conjugated polyclonal goat anti-mouse immunoglobulin antibodies for 120 minutes at 37° C. Finally, the plates are washed with distilled water (5 times), and developed with 3,5,3',5'-tetramethyl benzidine. Anti-factor XI antibodies obtained in this way are further analyzed. This assay is referred to as assay 6 in Table 2, the denotation is FXI/FXIa when a mAb binds to factor XI and factor XIa when tested in these ELISAs; FXI when only binding to factor XI and not to factor XIa; and FXIa when the monoclonal antibody only binds to factor XIa and not to factor XI.

Example 7

Preparation of Purified Monoclonal Antibody Anti-Factor XI

Antibody is produced in vitro from the hybridoma anti-factor XI or XIa by culturing the cells in 1 liter roller-bottles in Iscove's Modified Dulbecco medium supplemented with 2% (v/v) fetal calf serum, 10 pg/ml IL-6, 50 μM 2-mercaptoethanol, and penicillin and streptomycin. The cells are grown to a density of >$10^6$ cells per ml, and one to two weeks later the supernatants are collected. Solid ammonium sulphate is added to yield 50% saturation (i.e., approximately 2M), and an antibody-enriched fraction is obtained by centrifugation for 30 minutes at 1,300 g. The precipitate is dissolved in 1.5 M NaCl/0.75 M glycine, pH 8.9, and put onto a protein A-Sepharose column (Pharmacia). The column is washed with PBS, and then anti-factor XI monoclonal antibody is eluted off with glycine-HCl, pH 2.5. Fractions are neutralised instantaneously with 2M TRIS, pH 8.0, and those containing protein are pooled and dialysed against PBS.

Example 8

Functional Characterization of Anti-Facor XI or XIa Monoclonal Antibodies

Antibodies against factor XI are characterized by testing them in the assays described above. Outcome of these experiments is as shown in Table 2.

TABLE 2

Examples of characterization of monoclonal antibodies against factor XI

| | Assay # | | | | | | |
|---|---|---|---|---|---|---|---|
| mAb | 1 | 2 | 3 | 4 | 5 | 6 | Interpretation |
| 1 | (—) | (—) | (—) | (—) | (—) | FXI/FXIa | MAB binds to all forms of FXI; not suitable as inhibitor |
| 2 | (—) | (—) | (—) | (—) | (—) | FXI | MAB binds to native FXI; not suitable as inhibitor |
| 3 | (—) | (—) | (—) | (—) | (—) | FXIa | MAB binds to neo-epitope on FXIa; not suitable as inhibitor |
| 4 | Inhibits | Inhibits | Inhibits | Inhibits | Inhibits | FXI/FXIa | MAb binds to active site of FXI(a); inhibitor of FXI |
| 5 | (—) | Inhibits | (—) | Inhibits | (—) | FXI | MAb binds native FXI near to $Arg_{369}$-$Ile_{370}$; inhibitor of FXI |
| 6 | (—) | (—) | Inhibits | Inhibits | Inhibits | FXI/FXIa | MAb binds to FIX binding site of FXI; inhibitor |

TABLE 2-continued

Examples of characterization of monoclonal antibodies against factor XI

| mAb | Assay # | | | | | | Interpretation |
|---|---|---|---|---|---|---|---|
| | 1 | 2 | 3 | 4 | 5 | 6 | |
| 7 | (—) | (—) | (—) | Inhibits | Inhibits | FXI/FXIa | MAb binds to HK binding site of FXI; potential inhibitor |
| 8 | (—) | Inhibits | Inhibits | Inhibits | Inhibits | FXIa | MAb binds to neo-epitope near to active site; inhibitor |

(—) = no effect

For application as inhibitor several types of antibody are selected, referred to in the table as "inhibitor". Note that this table is not complete, other functional patterns may be encountered.

Example 9

Effects of Anti-Factor XI Monoclonal Antibody on Experimental Thrombosis in Mouse Model Efficacy of anti-factor XI monoclonal antibody to attenuate or prevent thrombosis in vivo is studied in factor XI knockout mice (D Gailani et al., Blood Coagul. Fibrinolysis. 1997; 8:134-144), which are supplemented with human factor XI. The animals are then subjected to experimental thrombus formation induced by $FeCl_3$-induced injury, for example as described by T Renné et al., J Exp Med 2005; 202:271-281. Briefly, 4-5-wk-old mice are anesthetized by i.p. injection of 2,2,2-tribromoethanol and 2-methyl-2-butanol (0.15 ml/10 g of body weight from a 2.5% solution; Sigma-Aldrich). Human factor XI (for example 0.2 mg/kg) is injected via the tail vein, shortly before the experiment is started. 10e8 CFSE-labeled platelets per mouse are injected via the tail vein as a second injection. Monoclonal antibody against human factor XI is administered either together with, before or after the injection of human factor XI at a dose of 0.5-10 mg/kg. The mesentery is externalized through a midline abdominal incision. 35-60-μm-diameter arterioles are visualized at 10× with an inverted microscope (Axiovert 200; Carl Zeiss MicroImaging, Inc.) equipped with a 100-W fluorescent lamp source (HBO) and a CCD camera (CV-M300; Visitron Systems GmbH) connected to an S-VHS video recorder (AG-7355; Panasonic). After topical application of a filter paper (2×1 mm) saturated with 20% $FeCl_3$ for 1 min, arterioles are monitored for 40 min or until complete occlusion (blood flow stopped for >1 min) occurs. Platelet adhesion is defined as the number of fluorescently labeled platelets bound to the vessel wall 5 min after injury. A thrombus was defined as a platelet aggregate >20 μm in diameter. Efficacy of the monoclonal antibody to inhibit thrombus formation is shown by comparing results of mice supplemented with human factor XI only (thrombus formation; occlusion), human factor XI and anti-factor XI monoclonal antibody (no thrombus formation; no occlusion), or not supplemented at all (no thrombus formation; no occlusion), and wild-type mice (thrombus formation; occlusion).

Example 10

Effects of Anti-Factor XI Monoclonal Antibody on a Primate Model for Experimental Thrombosis Efficacy of anti-factor XI monoclonal antibody to attenuate or prevent thrombosis in vivo is also studied in non-human primate models for thrombosis, for example the models as described by A Gruber et al. (Blood. 2003; 102:953-955). Briefly, baboons are appropriately anaestesized and injected intravenously with intravenous porcine heparin (1000 U/mL; Wyeth-Ayerst, Pearl River, N.Y.) as an anti-coagulant control or affinity-purified monoclonal antibody against factor XI at a dose of 0.5-10 mg per kg. In addition, some animals do not receive heparin or anti-factor XI monoclonal antibody. The antithrombotic effects of heparin or anti-factor XI monoclonal antibody are studied using thrombogenic devices deployed for 60 minutes into surgically placed high flow chronic arteriovenous (AV) shunts. The device to be used can be a 20-mm long dacron graft segment (0.25 mL) and a silicone extension chamber (1.3 mL), or a 20-mm long (0.25 mL) ringed expanded polytetrafluoroethylene (ePTFE, teflon) graft segments (WL Gore, Newark, Del.) in the shunt. The hypothrombogenic ePTFE graft is converted into an acutely thrombogenic tissue factor-dependent device as described by Gruber et al. Prior to deployment, the graft is rinsed by passing 50 mL saline through the lumen. Blood flow is kept at 100 mL/min by proximal clamping. Thrombogenesis is assessed by measuring radiolabeled fibrin and platelet contents of the thrombogenic devices. In brief, the terminal fibrin content of graft/chamber thrombi (fibrin deposition) was determined by direct $^{125}$Iodine-labeled fibrin counting. The number of deposited platelets in 35-cm long 4-mm internal diameter shunt segments that incorporate the devices and associated thrombi is quantified by $^{111}$Indium-labeled platelet imaging with 5-minute data acquisition periods. Net platelet accumulation rate (NPAR) is calculated as the change in the platelet content of the device within one period.

Those skilled in the art will recognize or be able to ascertain, using routine experimentation, many equivalents of the specific embodiments of the invention described herein. Such equivalents are intended to be encompassed by the following claims. Any combination of the embodiments disclosed in the dependent claims is also contemplated to be within the scope of the invention.

What is claimed is:

1. A monoclonal antibody (mAb) or a Factor XI-binding binding fragment thereof, that binds Factor XI and inhibits Factor XI activation, which antibody or fragment binds at or near the peptidyl bond Arg369-Ile370 in Factor XI, thereby preventing cleavage of the bond and said activation, wherein said mAb or fragment, when administered to a subject in an effective amount, treats or attenuates a thrombo-embolic disease.

2. The mAb or fragment according to claim 1, that treats or attenuates said disease, when administered at a dosage equivalent to a dosage of 0.5-20 mg of IgG per kg body weight.

3. The mAb molecule or fragment according to claim 1, that treats or attenuates said disease when administered at a dosage that yields a molar ratio in serum that is equal to or less than 4 moles of factor XI binding sites to 1 mole of factor XI, wherein the antibody or fragment has an affinity for factor XI characterized as a Kd that is equal to or less than 1 nM.

4. The mAb or fragment according to claim 1, wherein the thrombo-embolic disease treated or attenuated is ischemic stroke, cardioembolism, vascular access thrombosis, deep venous thrombosis, diffuse intravascular coagulation, sepsis, or septic shock.

5. The mAb or fragment according to claim 1, that treats or attenuates said disease when administered intravenously, intramuscularly or subcutaneously.

6. The mAb or fragment according to claim 5, that treats or attenuates said disease when administered intravenously as a bolus infusion or as a continuous infusion over an interval of up to 24 hours.

7. The mAb or fragment according to claim 1, that has a half life of at least 6 days when administered and an affinity for Factor XI characterized by a Kd that is less than 1 nM.

* * * * *

SEQUENCE LISTING

<160> NUMBER OF SEQ ID NOS: 1

<210> SEQ ID NO 1
<211> LENGTH: 607
<212> TYPE: PRT
<213> ORGANISM: Homo sapiens

<400> SEQUENCE: 1

```
Glu Cys Val Thr Gln Leu Leu Lys Asp Thr Cys Phe Glu Gly Gly Asp
 1               5                  10                  15

Ile Thr Thr Val Phe Thr Pro Ser Ala Lys Tyr Cys Gln Val Val Cys
            20                  25                  30

Thr Tyr His Pro Arg Cys Leu Leu Phe Thr Phe Thr Ala Glu Ser Pro
        35                  40                  45

Ser Glu Asp Pro Thr Arg Trp Phe Thr Cys Val Leu Lys Asp Ser Val
 50                  55                  60

Thr Glu Thr Leu Pro Arg Val Asn Arg Thr Ala Ala Ile Ser Gly Tyr
 65                  70                  75                  80

Ser Phe Lys Gln Cys Ser His Gln Ile Ser Ala Cys Asn Lys Asp Ile
                85                  90                  95

Tyr Val Asp Leu Asp Met Lys Gly Ile Asn Tyr Asn Ser Ser Val Ala
            100                 105                 110

Lys Ser Ala Gln Glu Cys Gln Glu Arg Cys Thr Asp Asp Val His Cys
            115                 120                 125

His Phe Phe Thr Tyr Ala Thr Arg Gln Phe Pro Ser Leu Glu His Arg
130                 135                 140

Asn Ile Cys Leu Leu Lys His Thr Gln Thr Gly Thr Pro Thr Arg Ile
145                 150                 155                 160

Thr Lys Leu Asp Lys Val Val Ser Gly Phe Ser Leu Lys Ser Cys Ala
                165                 170                 175

Leu Ser Asn Leu Ala Cys Ile Arg Asp Ile Phe Pro Asn Thr Val Phe
            180                 185                 190

Ala Asp Ser Asn Ile Asp Ser Val Met Ala Pro Asp Ala Phe Val Cys
            195                 200                 205

Gly Arg Ile Cys Thr His His Pro Gly Cys Leu Phe Phe Thr Phe Phe
210                 215                 220

Ser Gln Glu Trp Pro Lys Glu Ser Gln Arg Asn Leu Cys Leu Leu Lys
225                 230                 235                 240

Thr Ser Glu Ser Gly Leu Pro Ser Thr Arg Ile Lys Lys Ser Lys Ala
                245                 250                 255

Leu Ser Gly Phe Ser Leu Gln Ser Cys Arg His Ser Ile Pro Val Phe
            260                 265                 270

Cys His Ser Ser Phe Tyr His Asp Thr Asp Phe Leu Gly Glu Glu Leu
        275                 280                 285

Asp Ile Val Ala Ala Lys Ser His Glu Ala Cys Gln Lys Leu Cys Thr
290                 295                 300

Asn Ala Val Arg Cys Gln Phe Phe Thr Tyr Thr Pro Ala Gln Ala Ser
305                 310                 315                 320

Cys Asn Glu Gly Lys Gly Lys Cys Tyr Leu Lys Leu Ser Ser Asn Gly
                325                 330                 335

Ser Pro Thr Lys Ile Leu His Gly Arg Gly Gly Ile Ser Gly Tyr Thr
            340                 345                 350

Leu Arg Leu Cys Lys Met Asp Asn Glu Cys Thr Thr Lys Ile Lys Pro
            355                 360                 365

Arg Ile Val Gly Gly Thr Ala Ser Val Arg Gly Glu Trp Pro Trp Gln
370                 375                 380

Val Thr Leu His Thr Thr Ser Pro Thr Gln Arg His Leu Cys Gly Gly
385                 390                 395                 400

Ser Ile Ile Gly Asn Gln Trp Ile Leu Thr Ala Ala His Cys Phe Tyr
                405                 410                 415
```

-continued

```
Gly Val Glu Ser Pro Lys Ile Leu Arg Val Tyr Ser Gly Ile Leu Asn
            420             425             430

Gln Ser Glu Ile Lys Glu Asp Thr Ser Phe Phe Gly Val Gln Glu Ile
            435             440             445

Ile Ile His Asp Gln Tyr Lys Met Ala Glu Ser Gly Tyr Asp Ile Ala
    450             455             460

Leu Leu Lys Leu Glu Thr Thr Val Asn Tyr Thr Asp Ser Gln Arg Pro
465             470             475             480

Ile Cys Leu Pro Ser Lys Gly Asp Arg Asn Val Ile Tyr Thr Asp Cys
            485             490             495

Trp Val Thr Gly Trp Gly Tyr Arg Lys Leu Arg Asp Lys Ile Gln Asn
            500             505             510

Thr Leu Gln Lys Ala Lys Ile Pro Leu Val Thr Asn Glu Glu Cys Gln
            515             520             525

Lys Arg Tyr Arg Gly His Lys Ile Thr His Lys Met Ile Cys Ala Gly
            530             535             540

Tyr Arg Glu Gly Gly Lys Asp Ala Cys Lys Gly Asp Ser Gly Gly Pro
545             550             555             560

Leu Ser Cys Lys His Asn Glu Val Trp His Leu Val Gly Ile Thr Ser
            565             570             575

Trp Gly Glu Gly Cys Ala Gln Arg Glu Arg Pro Gly Val Tyr Thr Asn
            580             585             590

Val Val Glu Tyr Val Asp Trp Ile Leu Glu Lys Thr Gln Ala Val
            595             600             605
```